(12) United States Patent
Grum-Schwensen

(10) Patent No.: US 8,821,463 B2
(45) Date of Patent: Sep. 2, 2014

(54) DRAINABLE OSTOMY POUCH

(75) Inventor: Christen Grum-Schwensen, Hillerød (DK)

(73) Assignee: Hollister Incorporated, Libertyville, IL (US)

(*) Notice: Subject to any disclaimer, the term of this patent is extended or adjusted under 35 U.S.C. 154(b) by 42 days.

(21) Appl. No.: 13/255,802

(22) PCT Filed: Mar. 16, 2010

(86) PCT No.: PCT/EP2010/053327
§ 371 (c)(1),
(2), (4) Date: Oct. 12, 2011

(87) PCT Pub. No.: WO2010/106036
PCT Pub. Date: Sep. 23, 2010

(65) Prior Publication Data
US 2012/0022477 A1  Jan. 26, 2012

(30) Foreign Application Priority Data

Mar. 17, 2009 (EP) .................................... 09155337

(51) Int. Cl.
*A61F 5/44* (2006.01)
(52) U.S. Cl.
USPC ........................................................ 604/332
(58) Field of Classification Search
USPC ........................................................ 604/332
See application file for complete search history.

(56) References Cited

U.S. PATENT DOCUMENTS

| | | | |
|---|---|---|---|
| 2,520,831 | A | 8/1950 | Chincholl |
| 2,782,785 | A | 2/1957 | Arcand |
| 3,189,253 | A | 6/1965 | Mojonnier |
| 3,251,390 | A | 5/1966 | Evans |
| 3,406,853 | A | 10/1968 | McLeod |
| 3,408,705 | A | 11/1968 | Kayser et al. |
| 3,473,532 | A | 10/1969 | Eisenberg |

(Continued)

FOREIGN PATENT DOCUMENTS

| | | |
|---|---|---|
| DE | 29 36 622 A1 | 3/1981 |
| EP | 1 378 218 A1 | 1/2004 |

(Continued)

OTHER PUBLICATIONS

International Search Report, mailed Jan. 7, 2010 (3 pages).

(Continued)

*Primary Examiner* — Susan Su
*Assistant Examiner* — Guy K Townsend
(74) *Attorney, Agent, or Firm* — Levenfeld Pearlstein, LLC

(57) ABSTRACT

The present invention concerns a drainable ostomy pouch comprising first proximal pouch wall and second distal pouch wall joined together along the outer periphery to form a cavity for accommodating waste material and to form an outlet portion with an outlet for draining the content of the pouch; an inlet provided in the first pouch wall for receiving waste into the pouch; a comfort layer provided at least on the distal side wall; a closure system with first and second fastener strips provided on at least one, preferably both exterior sides of the pouch walls for in cooperation to close the outlet by folding the outlet portion upon itself, wherein the second fastener strip is provided between the comfort layer and the distal side wall such that the outlet portion when folded up may be releasably secured to the comfort layer between the comfort layer and the distal side wall.

17 Claims, 3 Drawing Sheets

(56) References Cited

U.S. PATENT DOCUMENTS

| | | | |
|---|---|---|---|
| 3,507,282 | A | 4/1970 | Burding |
| 3,523,534 | A | 8/1970 | Nolan |
| 3,567,074 | A | 3/1971 | Brown |
| 3,688,973 | A | 9/1972 | Salomo Lillkvist |
| 3,690,320 | A | 9/1972 | Riely |
| 3,724,461 | A | 4/1973 | Eisenberg |
| 3,734,154 | A | 5/1973 | Polk |
| 3,825,005 | A | 7/1974 | Fenton |
| 3,897,780 | A | 8/1975 | Trousil |
| 3,924,631 | A | 12/1975 | Mancusi, Jr. |
| 4,050,468 | A | 9/1977 | Wynnyk |
| 4,230,115 | A | 10/1980 | Walz, Jr. et al. |
| 4,233,977 | A | 11/1980 | Mattson |
| 4,310,952 | A | 1/1982 | Robben et al. |
| 4,411,659 | A | 10/1983 | Jensen et al. |
| 4,439,191 | A | 3/1984 | Hogan |
| 4,441,659 | A | 4/1984 | Marklund |
| 4,460,359 | A | 7/1984 | Fenton |
| 4,465,486 | A | 8/1984 | Hill |
| 4,561,540 | A | 12/1985 | Hunter et al. |
| 4,596,566 | A | 6/1986 | Kay |
| 4,686,814 | A | 8/1987 | Yanase et al. |
| 4,755,177 | A | 7/1988 | Hill |
| 4,838,874 | A | 6/1989 | Eisenberg |
| 4,846,820 | A * | 7/1989 | Jensen ............ 604/339 |
| 4,869,725 | A | 9/1989 | Schneider et al. |
| 4,898,477 | A | 2/1990 | Cox et al. |
| 4,983,172 | A | 1/1991 | Steer et al. |
| 4,988,343 | A | 1/1991 | Ballan et al. |
| 5,000,500 | A | 3/1991 | Almog et al. |
| 5,030,211 | A | 7/1991 | Zakroczymski |
| 5,037,138 | A | 8/1991 | McClintock et al. |
| 5,037,149 | A | 8/1991 | Beck |
| 5,044,774 | A | 9/1991 | Bullard et al. |
| 5,174,658 | A | 12/1992 | Cook et al. |
| 5,184,896 | A | 2/1993 | Hammond et al. |
| 5,457,855 | A | 10/1995 | Kenney et al. |
| 5,520,670 | A * | 5/1996 | Blum ............ 604/338 |
| 5,545,154 | A | 8/1996 | Oberholtzer |
| D379,654 | S | 6/1997 | Holtermann |
| 5,643,234 | A | 7/1997 | Lesko |
| 5,647,670 | A | 7/1997 | Iscovich |
| 5,690,621 | A | 11/1997 | Canela |
| 5,745,926 | A | 5/1998 | Cailleteau |
| 5,941,640 | A | 8/1999 | Thatcher |
| 5,968,023 | A | 10/1999 | Olsen |
| 5,968,024 | A | 10/1999 | Freeman |
| 6,212,716 | B1 | 4/2001 | Logan, Jr. et al. |
| 6,267,506 | B1 | 7/2001 | Campion |
| 6,336,918 | B1 | 1/2002 | Olsen et al. |
| 6,419,664 | B1 | 7/2002 | von Bulow et al. |
| 6,544,241 | B2 | 4/2003 | Morton |
| 6,589,221 | B1 | 7/2003 | Olsen et al. |
| 6,644,854 | B2 | 11/2003 | Lien |
| 6,726,667 | B2 | 4/2004 | Leise, Jr. et al. |
| 6,780,172 | B2 | 8/2004 | Olsen et al. |
| 6,858,023 | B2 | 2/2005 | Poulsen |
| 6,887,222 | B2 | 5/2005 | Mandzij et al. |
| 7,223,260 | B2 | 5/2007 | Hansen et al. |
| 7,306,581 | B2 | 12/2007 | Falconer et al. |
| 7,468,056 | B2 | 12/2008 | Burt |
| 7,722,585 | B2 | 5/2010 | Falconer et al. |
| D618,791 | S | 6/2010 | Schena |
| 7,879,015 | B2 * | 2/2011 | Villefrance et al. ............ 604/332 |
| 7,947,025 | B2 * | 5/2011 | Buglino et al. ............ 604/335 |
| 2001/0037627 | A1 | 11/2001 | Hausslein |
| 2002/0010444 | A1 | 1/2002 | Wiltshire et al. |
| 2002/0111659 | A1 | 8/2002 | Davis et al. |
| 2002/0165507 | A1 | 11/2002 | Hessel et al. |
| 2003/0028160 | A1 | 2/2003 | Leise et al. |
| 2003/0073962 | A1 | 4/2003 | Olsen et al. |
| 2003/0167042 | A1 | 9/2003 | Poulsen |
| 2004/0049837 | A1 | 3/2004 | Falconer et al. |
| 2004/0059306 | A1 * | 3/2004 | Tsal et al. ............ 604/332 |
| 2005/0131360 | A1 | 6/2005 | Villefrance et al. |
| 2005/0159717 | A1 | 7/2005 | Holtermann |
| 2005/0283126 | A1 | 12/2005 | Schena et al. |
| 2006/0015079 | A1 | 1/2006 | Mandzij et al. |
| 2006/0111682 | A1 | 5/2006 | Schena et al. |
| 2007/0265588 | A1 | 11/2007 | Pedersen |
| 2008/0033379 | A1 | 2/2008 | Pedersen |
| 2008/0051743 | A1 * | 2/2008 | Falconer et al. ............ 604/332 |
| 2008/0097360 | A1 | 4/2008 | Andersen et al. |
| 2008/0226864 | A1 | 9/2008 | Willis et al. |
| 2008/0269699 | A1 | 10/2008 | O'Toole |
| 2008/0269700 | A1 | 10/2008 | O'Toole et al. |
| 2009/0043271 | A1 | 2/2009 | Winther |
| 2009/0082743 | A1 | 3/2009 | Buglino et al. |
| 2009/0143755 | A1 | 6/2009 | Schertiger |
| 2009/0192479 | A1 | 7/2009 | Schertiger |
| 2009/0234312 | A1 | 9/2009 | O'Toole et al. |
| 2009/0247971 | A1 | 10/2009 | Schena et al. |

FOREIGN PATENT DOCUMENTS

| | | |
|---|---|---|
| EP | 1 832 256 A2 | 9/2007 |
| FR | 2 870 112 A1 | 11/2005 |
| GB | 2 000 683 A | 1/1979 |
| GB | 2 268 065 A | 1/1994 |
| GB | 2 346 328 A | 8/2000 |
| GB | 2 398 743 A | 9/2004 |
| GB | 2 414 677 A | 12/2005 |
| JP | 59-28052 U | 2/1984 |
| JP | 09-301386 A | 11/1997 |
| WO | WO-93/00056 A1 | 1/1993 |
| WO | WO-96/19164 A1 | 6/1996 |
| WO | WO-98/53771 A1 | 12/1998 |
| WO | WO-99/25279 A1 | 5/1999 |
| WO | WO-99/66859 A2 | 12/1999 |
| WO | WO-01/28470 A1 | 4/2001 |
| WO | WO-01/51383 A1 | 7/2001 |
| WO | WO-01/54632 A1 | 8/2001 |
| WO | WO-03/065944 A1 | 8/2003 |
| WO | WO-2008/134334 A1 | 11/2008 |
| WO | WO-2010/077377 A1 | 7/2010 |

OTHER PUBLICATIONS

Written Opinion, mailed Jan. 7, 2010 (4 pages).

* cited by examiner

DRAINABLE OSTOMY POUCH

REFERENCE TO RELATED APPLICATIONS

This is the U.S. national phase of International Application No. PCT//EP2010/053327, filed Mar. 16, 1010, which claims the priority benefit of European Patent Application No. EP 09155337.0, filed Mar. 17, 2009, the entire respective disclosures of which are incorporated herein by reference.

The present invention relates to a drainable ostomy pouch with a releasable sealable fold-up closure system.

In the art it is well known to provide drainable ostomy pouches with closure systems, where a downwardly extending outlet portion is closed by folding the outlet portion upwardly.

An example of such fold-up closure system is known from WO 2008/134334 where a resealable press and seal material is provided on the surface of the outlet portion so that the outlet portion is sealed and secured to itself when rolled up.

In the collecting bag described in WO 96/19164, the outlet section can be rolled up and closed by two closure clips which are folded from the sides of the outlet and with locking elements thereon to engage and secure the rolled up outlet section.

In WO 03/065944, there is described an ostomy pouch where a first fastening strip is located along the outer surface of a first side of the outlet portion and a second fastening strip is located along a second side of the outlet portion. When the outlet portion is folded up, the two fastening strips will eventually engage and thereby the outlet portion is fully folded and locked in a closed position.

Another solution is for instance shown in EP 1 378 218 A1, where one of the fastener parts is provided on a security flap which is secured under the downwardly oriented outlet portion and foldable to a position under the outlet when rolled up.

Common for all of these closure systems, there is a rolled up—or folded up—outlet portion as the lowermost point of the pouch during normal wear of the pouch. This folded/rolled up portion consists of multiple of layers of film material including outlet bias members and is therefore relatively stiff. This may result in discomfort for the user when using the pouch.

Accordingly, it is an object of the invention to provide a pouch with a closure system whereby the comfort when wearing the pouch is improved.

The invention concerns a drainable ostomy pouch comprising first proximal pouch wall and second distal pouch wall joined together along the outer periphery to form a cavity for accommodating waste material and to form an outlet portion with an outlet for draining the content of the pouch; an inlet provided in the first pouch wall for receiving waste into the pouch; a comfort layer provided at least on the distal side wall; a closure system with first and second fastener strips provided on at least one, preferably both exterior sides of the pouch walls for in cooperation to close the outlet by folding the outlet portion upon itself, wherein the second fastener strip is provided between the comfort layer and the distal side wall such that the outlet portion when folded up may be releasably secured to the comfort layer between the comfort layer and the distal side wall.

By the invention, the fold-up outlet portion is hidden behind the comfort layer or dressing panel and this makes the pouch more ergonomic to wear. The outlet portion is preferably folded up and hidden behind the comfort layer facing towards the skin of the user. By a pouch according to the invention, the amount of visual parts are reduced when the pouch is closed and thereby the appearance is more visually attractive as the pouch may be provided with a more discrete design which is beneficial to the user who wishes a minimum of interference with his or her normal life. Furthermore, there are fewer sharp edges on the pouch which can interfere with the user's clothing. For instance, there is no stiff fold-up extending downwardly from the pouch itself which may interfere with the user's clothing.

Another advantage by the pouch design is that the integrated fold-up closure system makes the pouch simple to manufacture and thereby allows for lower production costs compared with the ostomy pouches of this kind known in the art.

Preferably, the comfort layer is a non-woven material. However, it is realized that other types of material, such as film, fabric, or the like may be used as dressing panel or comfort layer.

According to the preferred embodiment, the second fastener strip is provided on the inside surface of the comfort layer. Moreover, the comfort layer is preferably provided with a reinforcement strip on which the second fastener strip is provided. Hereby, any risk of damaging the comfort layer when e.g. releasing the closure system is reduced. As an example the reinforcement strip may be made of a material similar to that of the wall panels forming the pouch.

In an embodiment the second fastener strip is provided on an extension of the comfort layer, and in particular the extension is provided on the distal side wall provided with a comfort layer material. This extension may be attached directly onto the distal wall panel of the pouch either by a linear attachment or by discrete attachments at the sides, for instance by providing the extension with a size so that its lateral extension overlaps the peripheral weldings. Preferably, the extension is a laminate and it also extends sufficiently downwardly to accommodate the folded up outlet portion.

In the closure system, the fastener strips may provide a peelable fastener system for releasably attaching and detaching the fold-up outlet portion. In particular, the first and second fastener strips may adhere to each other by mechanical engagement. As an example thereof the fastener system of the first and second fastener strips may be hook-hook type plastic extrusions, such as mushroom tip projections, for snap engagement between the two strips. Alternatively, the fastener system of the first and second fastener strips is hook and loop type fastener strips for snap engagement. Adhesive fasteners may also be used. Hereby, a simple and reliable fastening system is provided.

The pouch is welded along its periphery and preferably the outlet portion is formed such that the outlet portion comprises substantially parallel peripheral welding portions at a predetermined distance thereby defining the width of the outlet portion. In order to avoid residues of waste material in the pouch, there may be provided weldings defining the entry into the outlet portion. Accordingly, above the outlet portion the peripheral welding further includes inwardly extending welding portions on each side of the pouch where the distance between the two oppositely situated inwardly extending welding portions is equal to or less than the width of the outlet portion.

At the outlet edge, first and second bias members are preferably provided on each film transversely extending at the outlet periphery. The bias members are normally substantially flat so as to be in straight parallel closed condition but are openable under inwardly-directed finger pressure applied to their opposite ends to cause them to bow outwardly away from each other. The bias members may advantageously be aligned opposite each other at the outlet periphery or the bias members being shifted relative to each other so that the first bias member is provided at the periphery and the second bias member is provided adjacent said first bias member such that said first bias member may be folded to a position on top of the second bias member. Hereby, the outlet portion is more controllable during opening as the outlet drain is reinforced for a wider area at the outlet opening.

In the following the invention is described in further detail with reference to the accompanying drawings, in which FIG. 1 is a front view of an ostomy pouch according to a first embodiment of the invention;

Figures 1, 2:
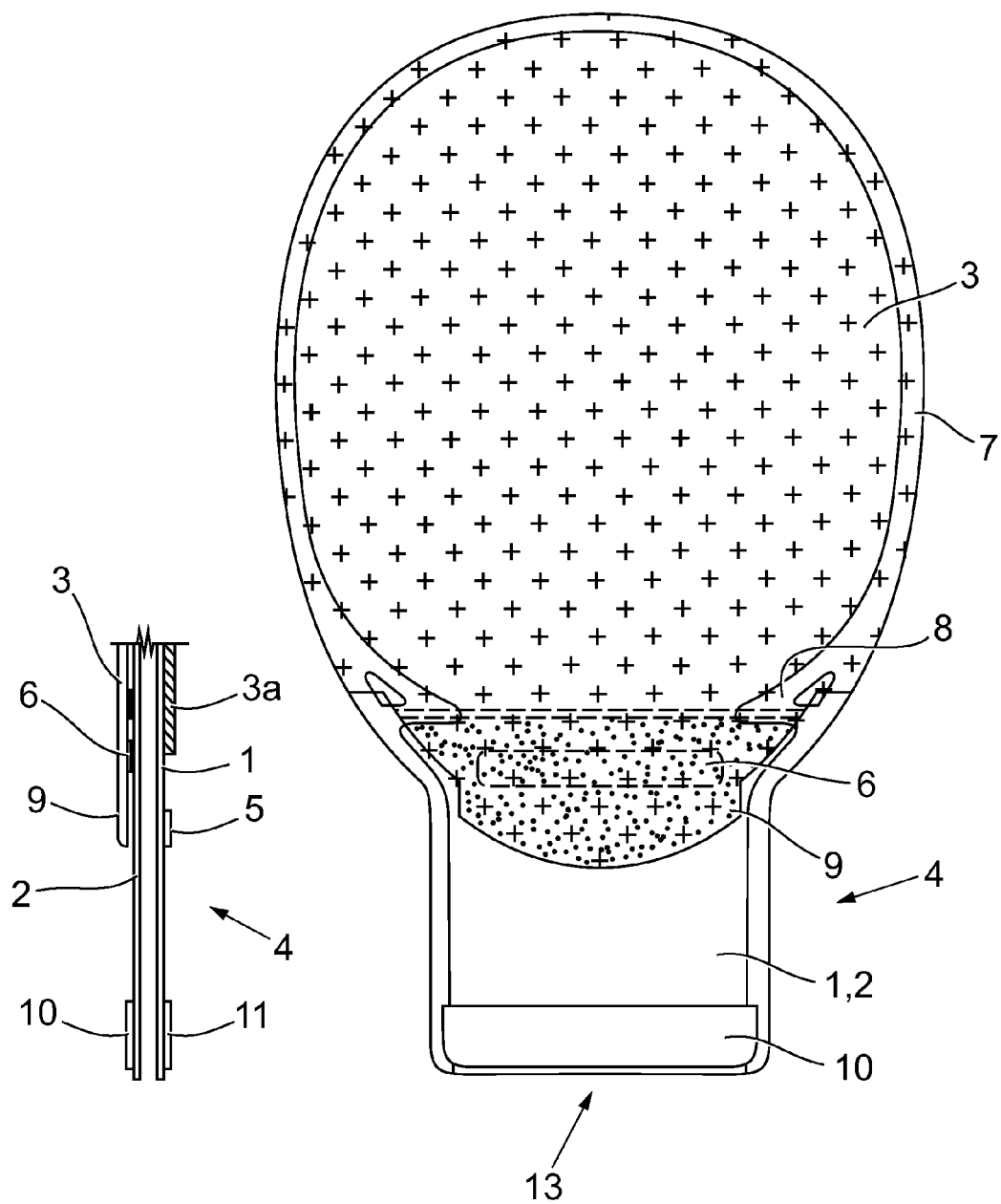
FIG. 2 is a schematic cross-section view of the outlet portion of the pouch in FIG. 1.

With reference to the figures, the drainable ostomy pouch is an assembly of two sidewalls 1 and 2 where the proximal sidewall 1 is provided with an inlet (not shown) and the distal sidewall 2 which according to the embodiment shown is provided with a dressing panel or comfort layer 3. As indicated in FIG. 2, a comfort layer 3a may also be provided on the proximal side of the pouch. The sidewalls 1, 2 as well as the comfort layer 3 are joined along their edges by a peripheral welding 7 to form a cavity between the two sidewalls 1, 2. The sidewalls 1, 2 are formed with a main portion for providing the cavity for accommodating waste material entering the pouch and with a downwardly extending outlet portion 4 which terminate in a discharge opening 13. The peripheral welding 7 accordingly leaves the discharge opening without any welding. The peripheral welding 7 is thus formed with a horseshoe-like form defining and following the contour of the pouch.

As shown in the figures, the outlet portion 4 is provided with a transversely extending bias member 10 and 11 on each of the two sidewalls 1, 2. The bias members 10, 11 are preferably in the form of relative stiff but flexible, spring-like strips. The bias members 10, 11 may be flat or slightly curved when they are in their resting position abutting each other. In order to facilitate the opening, the flat or slightly curved bias members 10, 11 may be provided with score lines (not shown).

The comfort layer 3 is designed to cover the main portion of the pouch whereas the outlet portion 4 extends downwardly from under the comfort layer 3 when the pouch is open for drainage. The comfort layer 3 is provided with an extension 9. On the proximal side of the proximal sidewall 1 there is provided a first fastener strip 5 in a predetermined distance from the discharge opening 13. On the inside surface of the extension 9, i.e. on the side of the extension 9 facing towards the distal side wall 2 (see FIG. 2), there is provided a second fastener strip 6. The first and second fastener strips 5, 6 are designed to cooperate and are positioned such that when the outlet portion is folded up around the bias members 10, 11, the first and second fastener strips are brought into contact and the rolled up outlet portion is thereby retained in a releasable, closed and sealed upwardly folded position behind the extension 9 of the comfort layer 3.

Figure 5:
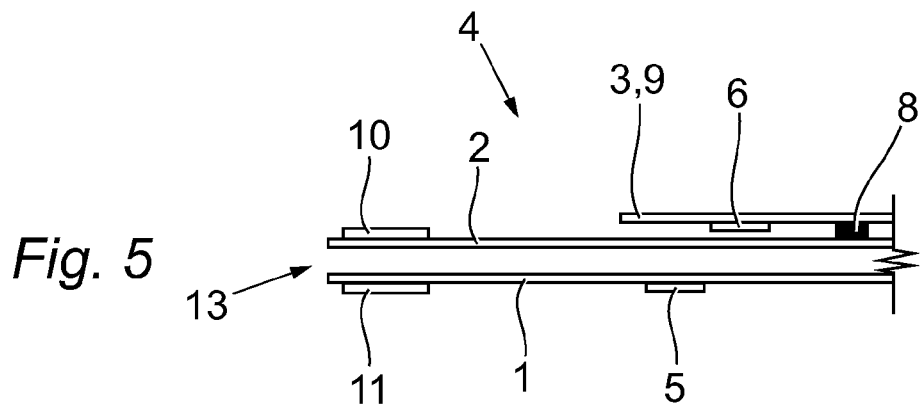
FIGS. 5 to 8 are cross-sectional schematic side views of the outlet portion of a pouch according to an embodiment of the invention and show the fold-up closure as it progresses.
Figure 6:
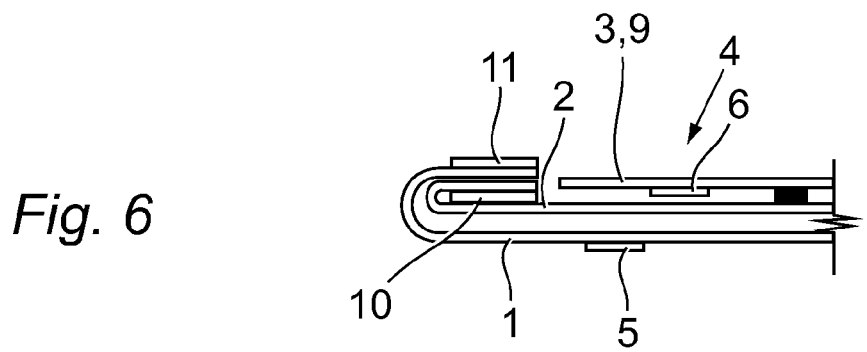
Figure 7:
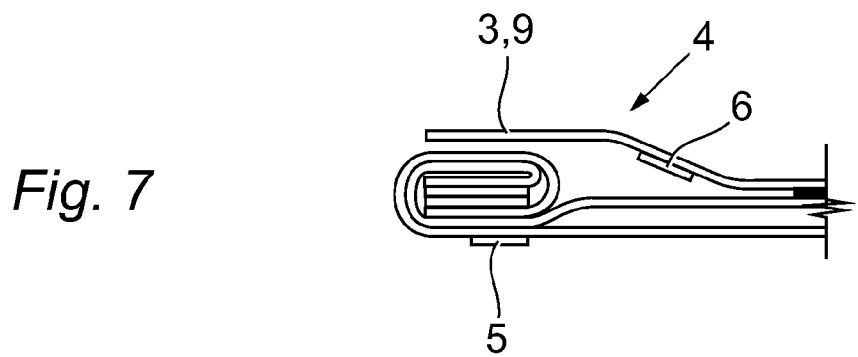
Figure 8:
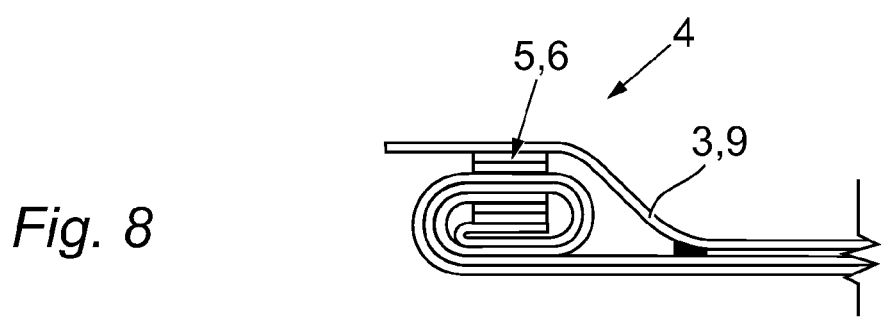

With reference to FIGS. 5 to 8, the fold-up closure process of the pouch is schematically illustrated. In FIG. 5 the pouch is open and as shown in FIG. 6, the outlet portion is then folded back around the bias members 10, 11 and folded again and again as shown in the FIGS. 7 and 8 until the first fastener strip 5 on the proximal side of the sidewall 1 by the folding is facing towards the distal side of the pouch and is brought into a position adjacent the second fastener strip 6 which is provided on the inside surface of the extension 9 of the comfort layer 3. As the first and second fastener strips 5, 6 are joined together the fold-up outlet portion is retained and the pouch is closed.

The sidewalls 1, 2 and the comfort layer 3 are preferably joined together in the same welding process where the peripheral welding 7 is applied including the inwardly protruding weldings 8 which are provided above the outlet portion 4 and the closure system. The outlet portion 4 is formed as an elongated downwardly extending portion with welding portions on either side what are substantially parallel. The inwardly protruding welding portions 8 define the passage between the cavity of the pouch and the outlet section of the pouch. The distance between these two inwardly pointing welding portions 8 is less than or equal to the width of the outlet portion 4.

The comfort layer 3 is preferably made of a non-woven material. In addition, the extension 9 may be provided with a reinforcement, e.g. a backing layer (not shown) holding the second fastener strip 6 in order to reduce the risk of damaging the comfort layer when using it as an active component in the pouch closure system.

Figures 3, 4:
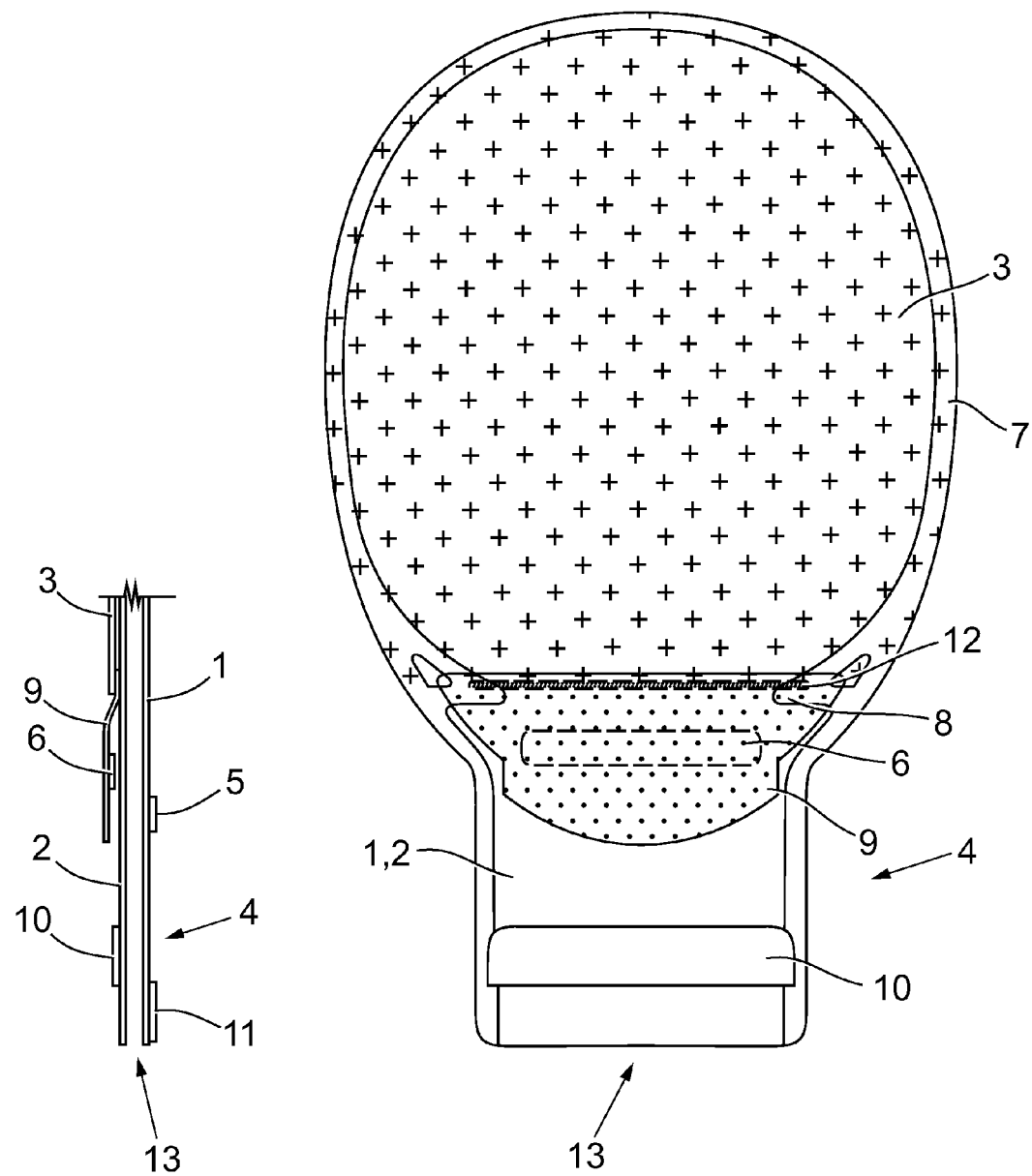
FIG. 3 is a front view of an ostomy pouch according to a second embodiment of the invention.
FIG. 4 is a schematic cross-section view of the outlet portion of the pouch in FIG. 3.

In FIGS. 3 and 4, another embodiment of the pouch is shown. According to this embodiment, the extension 9 is provided as a separate part which may be attached by being welded onto the pouch assembly during the welding and that the extension is attached to the pouch by the welding protrusions 8. In addition, a separate welding 12 may be provided for attaching the extension 9 to the distal side wall 2 prior to the joining of the layers 1, 2, 3 of the pouch. Alternatively, the extension 9 could be welded onto the comfort layer 3 prior to the pouch assembly welding process.

The outlet portion 4 formed in the sidewall panels 1, 2 below the welding protrusions 8 and the extension 9 is provided a width which is substantially the same along the outlet portion 4. Hereby, the outlet when folded up and secured and hidden behind the extension 9 is sealed.

As shown in FIGS. 3 and 4, the bias members 10, 11 at the discharge opening 13 can —as an alternative—be relatively displaced so that one of the bias members 11 is provided on the lower edge of the proximal sidewall 1 along the discharge opening 13 and the other bias member 10 is provided on the distal sidewall 2 in a distance from the discharge opening 13. This distance corresponds to the width of the bias members 10, 11 so that the first bias member 11 is folded along its upper edge and onto the second bias member 10. It is of cause realized that a pouch having this bias member configuration may be provided independent of the extension welding arrangement described above.

In the embodiments described above with reference to the figures, there is described a comfort layer on the distal side of the pouch. Alternatively, it is realized that the closure system could be provided with a comfort layer on the proximal side of the pouch as the active component. Moreover, in addition it is realized that comfort layers may be provided on both sides of the pouch to increase the comfort feel when using the pouch. Other variations may also be provided without departing from the scope of the invention.

The invention claimed is:
1. A drainable ostomy pouch comprising:
   a proximal pouch wall and a distal pouch wall joined together along an outer periphery of each to form a cavity for accommodating waste material and to form an outlet portion with an outlet for draining the content of the pouch;

an inlet provided in the first proximal pouch wall for receiving waste into the pouch;

a comfort layer provided at least on the distal pouch wall;

a closure system including first and second fastener strips for cooperatively closing the outlet by folding the outlet portion upon itself;

wherein the first fastener strip is provided on the proximal pouch wall; and the second fastener is provided between the comfort layer and the distal pouch wall such that the outlet portion when folded up may be releasably secured to the comfort layer between the comfort layer and the distal pouch wall, wherein the comfort layer remains unfolded, and the folded outlet portion is hidden behind the unfolded comfort layer.

2. A pouch according to claim 1, wherein the comfort layer is a non-woven film.

3. A pouch according to claim 1, wherein the second fastener strip is provided on an inside surface of the comfort layer.

4. A pouch according to claim 3, wherein the comfort layer is provided with a reinforcement strip on which the second fastener strip is provided.

5. A pouch according to claim 1, wherein the second fastener strip is provided on an extension of the comfort layer.

6. A pouch according to claim 5, wherein the extension is provided on the distal pouch wall provided with a comfort layer material.

7. A pouch according to claim 5, wherein the extension is a laminate.

8. A pouch according to claim 1, wherein the fastener strips provide a peelable fastener system for releasably attaching and detaching the fold-up outlet portion.

9. A pouch according to claim 1, wherein the first and second fastener strips adhere to each other by mechanical engagement.

10. A pouch according to claim 1, wherein the fastener system of the first and second fastener strips includes hook-hook type plastic extrusions, for snap engagement between the two strips.

11. A pouch according to claim 1, wherein the fastener system of the first and second fastener strips includes hook and loop type fastener strips for snap engagement.

12. A pouch according to claim 1, wherein the outlet portion comprises substantially parallel peripheral welding portions at a predetermined distance thereby defining a width of the outlet portion.

13. A pouch according to claim 1, wherein above the outlet portion the peripheral welding further includes inwardly extending welding portions on each side of the pouch where the distance between the two oppositely situated inwardly extending welding portions is equal to or less than a width of the outlet portion.

14. A pouch according to claim 1, wherein first and second bias members are provided on each film transversely extending at the outlet periphery.

15. A pouch according to claim 1, wherein said bias members are aligned opposite each other at the outlet periphery.

16. A pouch according to claim 1, wherein said bias members are shifted relative to each other so that the first bias members is provided at the periphery and the second bias member is provided adjacent said first bias member such that said first bias member may be folded to a position on top of the second bias member.

17. A pouch according to claim 10, wherein the hook-hook type plastic extrusions are mushroom tip projections.

* * * * *

UNITED STATES PATENT AND TRADEMARK OFFICE
CERTIFICATE OF CORRECTION

| | | |
|---|---|---|
| PATENT NO. | : 8,821,463 B2 | Page 1 of 1 |
| APPLICATION NO. | : 13/255802 | |
| DATED | : September 2, 2014 | |
| INVENTOR(S) | : Christen Grum-Schwensen | |

It is certified that error appears in the above-identified patent and that said Letters Patent is hereby corrected as shown below:

In the Claims

In Column 5, Claim 1, line 4, "first proximal" to read as --proximal--.

In Column 5, Claim 1, line 12 (approx.), "fastener" to read as --fastener strip--.

Signed and Sealed this
Twenty-fourth Day of February, 2015

Michelle K. Lee
*Deputy Director of the United States Patent and Trademark Office*